United States Patent [19]

Schultheiss et al.

[11] Patent Number: 5,531,751
[45] Date of Patent: Jul. 2, 1996

[54] AIMING TUBE ASSEMBLY

[75] Inventors: Rolf Schultheiss, Bonn; Gerhard Weber, Oberndorf, both of Germany

[73] Assignee: Gerhard Weber, Germany

[21] Appl. No.: 252,183

[22] Filed: Jun. 1, 1994

[30] Foreign Application Priority Data

Jun. 2, 1993 [DE] Germany ............................ 9308276 U

[51] Int. Cl.⁶ ............................ A61B 17/88; A61B 17/17
[52] U.S. Cl. .............................................. 606/96; 606/104
[58] Field of Search ................................ 606/96, 99, 104, 606/86, 79, 80, 73, 98; 403/83–85

[56] References Cited

U.S. PATENT DOCUMENTS

| | | | |
|---|---|---|---|
| 2,559,421 | 7/1951 | Garrett | 403/84 |
| 2,570,465 | 10/1951 | Lundholm | 606/73 |
| 4,722,331 | 2/1988 | Fox | 606/80 |
| 5,112,337 | 5/1992 | Paulos et al. | 606/98 |
| 5,176,681 | 1/1993 | Lawes et al. | 606/98 |
| 5,261,914 | 11/1993 | Warren et al. | 606/73 |
| 5,334,192 | 8/1994 | Behrens | 606/98 |

FOREIGN PATENT DOCUMENTS

| | | | |
|---|---|---|---|
| 81857 | 6/1983 | European Pat. Off. | 606/80 |
| 94371 | 6/1969 | France | 606/73 |
| 2679126 | 1/1993 | France | 606/79 |

OTHER PUBLICATIONS

Bohler, J. "Schraubenosteosynthese von Frakturen des Dens" (Screw Osteosynethesis of Fractures of the Dens Axis) Unfallheilkunde (Injury Treatment Science) 84 (1981), pp. 221–223.

Knoringer, P. "Zur Behandlung frischer Frakturen des Dens axis durch Compressionschrauben-osteosynthese" (Concerning the Treatment of Fresh Fractures of the Dens by Means of Compression Screw Osteosynthesis) Neurochirurgia 27 (1984), pp. 68–72.

Primary Examiner—Tamara L. Graysay
Attorney, Agent, or Firm—Dominik & Stein

[57] ABSTRACT

A device for facilitating the ventral screwing together of dens fractures with compression screws, characterized by a guide tube assembly comprised of two guide tube casings which are pivotably joined near one end by means of an articulated joint, and which are adjustable within a predetermined range of angles by an adjusting means. Bore wires, milling tools and compression screws can be introduced into the dens via the guide tube assembly at precise spatial and angular relationships set by the aiming tube assembly.

4 Claims, 3 Drawing Sheets

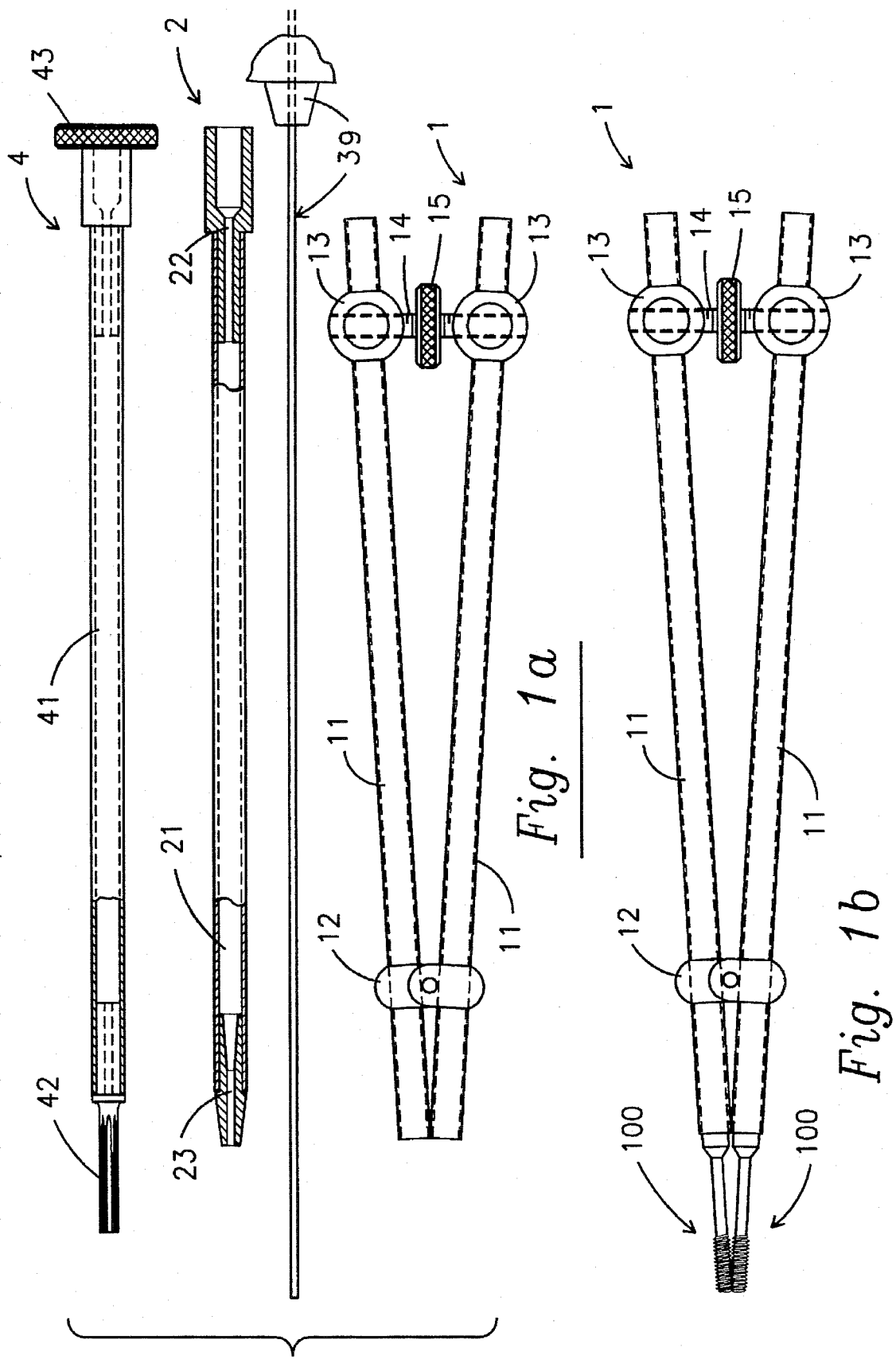

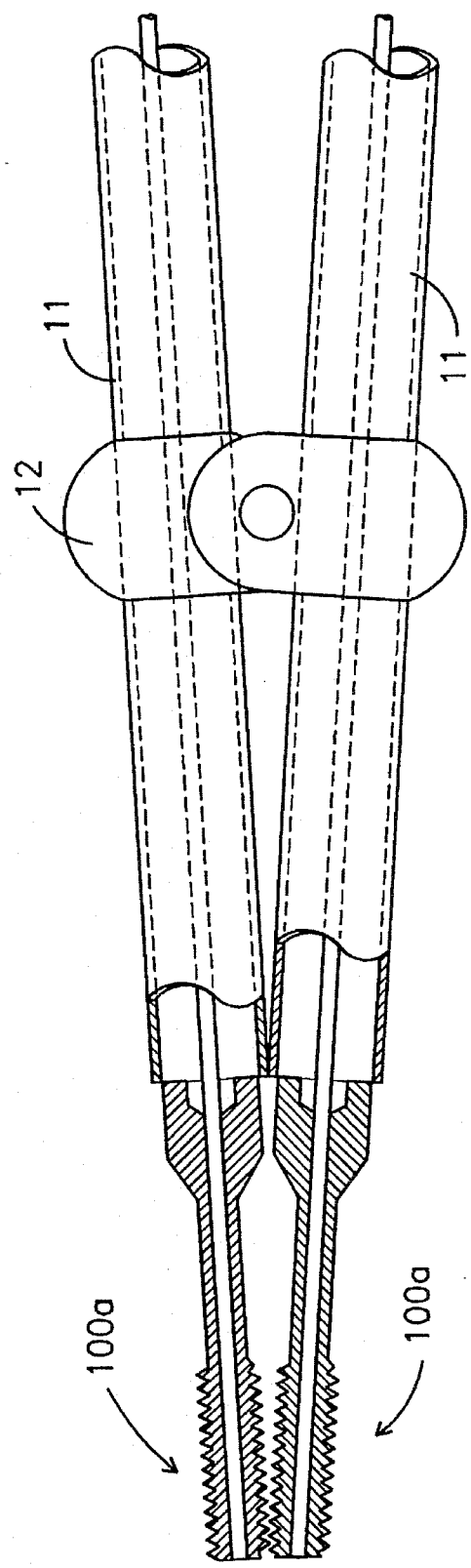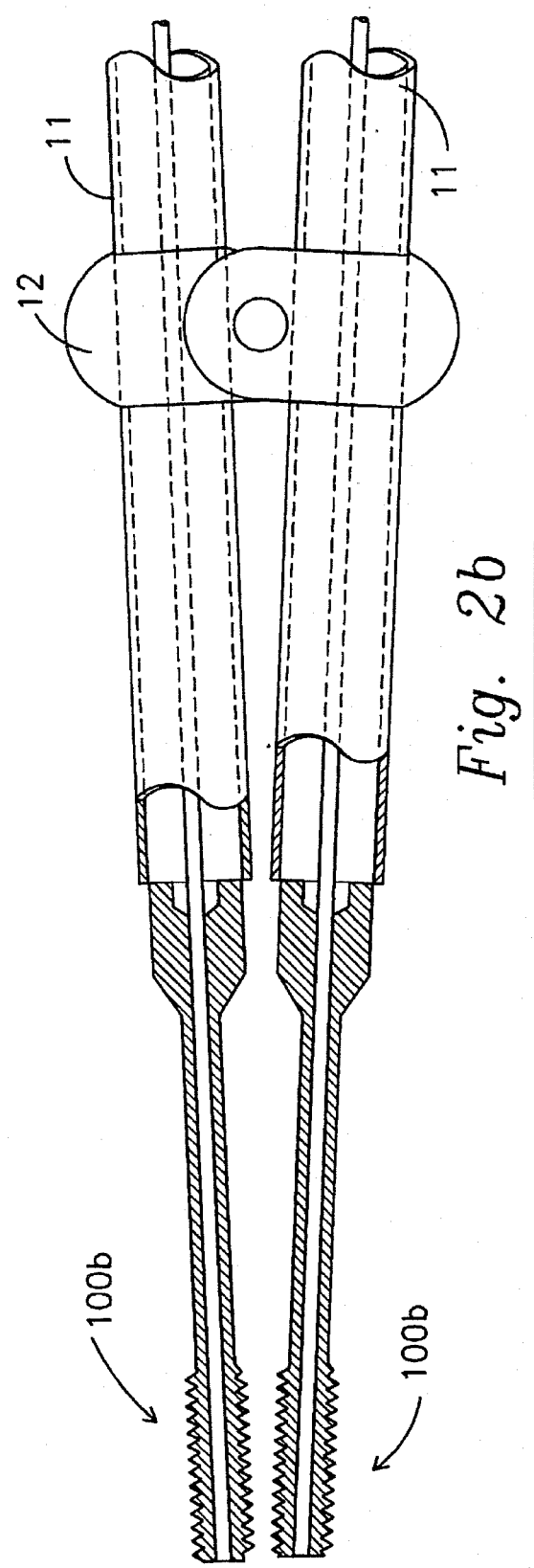

AIMING TUBE ASSEMBLY

BACKGROUND OF THE INVENTION

1. Field of the Invention

The invention concerns a device for facilitating the ventral screwing together of dens fractures with compression screws, characterized by a guide tube assembly comprised of two guide tube casings which are pivotably joined near one end by means of an articulated joint, and which are adjustable within a predetermined range of angles by an adjusting means. Bore wires, milling tools and compression screws can be introduced into the dens via the guide tube assembly at precise spatial and angular relationships set by the aiming tube assembly.

2. Description of the Related Art

Breaks in the dens, finger like projection of the second cervical vertebra, occur relatively frequently as a result of accidents involving the neck vertebrae. Processes have been devised for gaining frontal operational access to the cervical vertebrae for inserting screws to connect the fractured sections with each other. This type of process is often described in the literature, as for example the process according to Bohler, J. "Schraubenosteosynthese von Frakturen des Dens" (Screw Osteosynethesis of Fractures of the Dens) Unfallheilkunde (Injury Treatment Science) 84 (1981), pages 221–223 or a process according to Knoringer, P. "Zur Behaldlung frischer Frakturen des Dens axis durch Compressionschraubenosteosynthese" (Concerning the Treatment of Fresh Fractures of the Dens by Means of Compression Screw Osteosynthesis) Neurochirurgia 27 (1984), pages 68–72. The above described processes have been widely studied and have found acceptance in clinical practice.

When using the above mentioned surgical processes it is necessary to prepare a relatively large access opening from the front. Trachea as well as esophagus, as well as carotid arteries and jugular veins, are pushed out of the way and the neck soft parts are held aside by means of hooks. Guided by the aid of radiation imaging, boring wires (so-called churchmans wires) with a cross section of 0.5 mm are screwed into the neck vertebrae and the dens tip. Thereafter a milling cutter is slid coaxially over the boring wire and up to the entry point of the cervical vertebra. The milling cutter is used to create an insertion starting point at the entry point for a self cutting dens hollow screw. The dens hollow screw is slid over the bore wire after removal of the milling cutter and screwed into the cervical vertebrae. The dens hollow screw is constructed as a so-called compression screw, that is, it is provided with two different segments having different threads, so that upon the screwing in of the screw the two fragments are caused to be pulled towards each other and are finally held tightly pressed against each other. Hereby the two bone pieces are held in place.

For an optimal fixing of the two fragments it is necessary to implant two screws. The significance of the second screw is that it prevents the rotation of the two bone pieces with respect to each other. Only so is a connection of bones to be securely established. The implanting of the second screw, however, frequently is problematic, since the dens is relatively thin and therefore provides a severely limited working space. If the first screw is not properly placed, the insertion of a second screw is frequently precluded.

SUMMARY OF THE INVENTION

The invention is thus concerned with the problem of providing a device of the type which will be useful for the purposes of the above discussion of the related art, but which provides improved operational capabilities without suffering from the above described disadvantages.

The problem is solved by means of a device for ventral screwing together of dens fractures with compression screws, characterized by a guide tube assembly comprised of two guide tube casings which are pivotably joined by means of an articulated joint and which are precisely adjustable within a predetermined range of angles by means of an adjusting means. The angle between the two guide tube casings is precisely adjustable within a range of 4° to 6° by means of an adjusting means comprised of a threaded bolt with two counter rotating threaded sections which are respectively in engagement with threaded blocks provided on the guide tube casings. Further advantageous embodiments of the invention are set forth.

BRIEF DESCRIPTION OF THE DRAWINGS

The invention is described in greater detail by reference to the figures and the embodiment schematically represented therein. There is shown:

FIG. 1a side view, partially cut away, of the aiming tube assembly inclusive of the guiding casing, bore wire, and milling cutter, FIG. 1b side view, partially cut away, of the aiming tube assembly inclusive of the guiding casing and compression screws, FIG. 2a section from FIG. 1b with short compression screws and opening angle of 6°, FIG. 2b section from FIG. 1b with long compression screws and opening angle of 4°, FIG. 3 section from FIG. 1 (adjustment means), FIG. 4 cross-section 4—4 from FIG. 3.

DETAILED DESCRIPTION OF THE INVENTION

Figure 4:
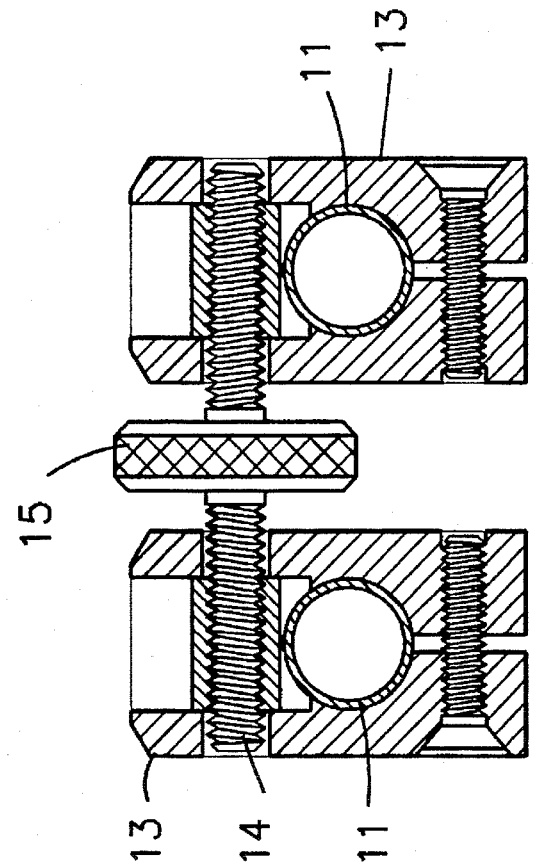

The invention is based upon the idea that it can be of great advantage during an operation of this type to have an operation assistance means in the form of an aiming tube assembly, which at least during the beginning of the screwing in process is guided and installed under radiation imaging control, but with which the remaining procedure however can proceed without constant picture imaging control. The aiming tube assembly is comprised essentially of two hollow aiming tube casings, which are pivotally connected by means of a swivel connection and which are precisely adjustable to a defined angle with respect to each other by means of an adjustment means.

The operation sequence is comprised as follows. First an incision is made in the skin on the right side of the front neck area, and the muscle sheath in front of the M. sternocleidomastoid is parted. Thereafter the trachea and the esophagus are pushed towards the center and the neck arteries and veins are pushed to the side. This can be accomplished, for example, by means of a dull trochar and an endoscope. The front surface of the second cervical vertebrae is located under x-ray imaging control, and the aiming tube assembly is placed in the middle thereof, whereby the aiming tube casings come to rest behind the front surface of the cervical vertebrae. The aiming tube assembly can be anchored in the desired position by means of a small point. Next the aiming tube is aligned with transillumination in the sagittal plane along the lengthwise body direction.

Next the actual bringing together of the fragments can be begun. For this purpose the bore wires are sequentially, with sideways transillumination, bored into the cervical vertebra body and into the dens tip. As a result of the angular orientation of the aiming tube casings the penetration direction of the bore wires is established.

After the bore wires have been introduced, the requisite length of the two dens screws can be determined by simple ways and means, such as by determining with a measuring template or other measuring device the length of the bore wire segments which extend out of the rear part of the aiming tube casing. Since the precise length of the aiming tube casings and the respective bore wires is known, it becomes possible to calculate the depth of penetration of the compression screw by subtraction of the length of the aiming tube casing and the length of the extending bore wire from the total bore wire length.

The compression screws are constructed with a coaxial bore, so that they can be guided over the bore wires and be screwed into the body of the cervical vertebra in the orientation which has been preordained by the bore wires. The compression screws are accordingly delivered to the place of insertion entirely within the aiming tube casings, without any direct contact with the neck soft parts. It is thus not necessary to prepare the surgical opening with the precondition of being able to visually monitor the introduction of the screws, rather it is sufficient to prepare the surgical opening in the manner of an endoscopic, minimally invasive process. It is also no longer necessary to remove the bore wires as in the conventional manner in order to determine the requisite screw length by measuring the bore canal directly. A further, more important advantage is therein to be seen, that the compression screws can be simultaneously or as the case may be alternatively successively tightened and that thereby the desired compression effect for the bringing together of the fragments by means of both screws simultaneously can be achieved.

An optimal precision, and at the same time a reduction in time, is achieved by special, assisting tools which are coordinated with the geometry of the aiming tube assembly.

So are envisioned guiding casings for the bore wires, which are matched to the cross section of the aiming tube casings and adapted to fit inside thereof. They are responsible for the guidance of the bore wire and assume an exact, coaxial orientation within the aiming tube casing and make possible the making of a bore in the direction which is predetermined by the orientation of the aiming tube casing. The guiding casings are removed from the aiming tube casings after the bore wires are inserted, whereupon the bore wire remains by itself for the time being in the aiming tube casing.

The insertion points for the compression screws can now be precut by means of a special milling cutter. The milling cutter likewise is provided with an axial continuous bore hole, so that it can be guided under the protection of the aiming tube casing over the bore wire to the point of insertion. The milling cutter extends rearward beyond the aiming tube casing of the aiming tube assembly and can be operated by means of a knurled wheel. After the production of the insertion point the milling cutter is removed from the aiming tube casing, so that finally the compression screws can be delivered by guiding over the bore wires.

The screws are at this time screwed in simultaneously or, as desired, successively. For operating, the compression screws are provided with the conventional internal six-sided opening, in which a correspondingly formed, likewise over the bore wire guided work tool engages.

The relative positioning, that is, the angle between the two aiming tube casings, can be precisely adjusted. The possible angles lie between 4° and 6°. This range of angles resulted from an analysis of the measurements of the dens given in the literature. The positioning possibilities, that is, the angles as well as the separation of the two screws to be provided, were derived in dependence on the geometry of the two compression screws to be implanted. In dependence upon the actual length of the dens, the angle is determined at which the compression screws, and thus the compression screw guiding bore wires, are to be placed in the fractured pieces. The determined angle can be precisely set by means of an adjustment means.

The invention will now be discussed with reference to the figures.

In FIG. 1a an aiming tube assembly 1 is comprised of two identical aiming tube casings 11, which by means of articulated joint 12 are pivotably connected with each other. The relative angle positions, which can be described by the two aiming tube casings, is precisely adjustable between 4° and 6°. The fine adjustment is accomplished by means of threaded bolt 14 which is provided with two outwardly directed, counter-rotating threaded segments and which threaded bolt is operable by hand by means of a knurled wheel 15 provided centrally. The counter-rotating threaded segments engage the threaded blocks 13, which are respectively securely mounted on the aiming tube casings 11. The angular position of 4° is determined by the abutting of the threaded blocks 13 on the surface of the knurled wheel 15, whereas on the other hand the angular position of 6° is defined by the internal binding of the threaded segment of the threaded bolt 14 in the threaded blocks 13. Thereby a definite and reliable limitation on the ranges of angular adjustments is built in.

In FIG. 2a,b there is shown in schematic representation the relationship of angular position and length of compression screws 100a,b. In the case of the short compression screw 100a shown in FIG. 2a a half-opening angle of 3° is shown, corresponding to a full angle of 6°. In FIG. 2b a long compression screw 100b is shown which has a relative angle corresponding to 4°.

In FIG. 1a a bore wire 3 is schematically represented, which is enclosed by a bore feeder 9 of a not shown bore machine. The guidance of the bore wire 3 within the guiding tube casing 11 is the responsibility of the guiding tube 2. It is comprised of a casing body 21 in the form of a tube, of which the outer diameter is made to correspond to the internal diameter of the aiming tube casing 11 in such a manner, that the guiding casing 2 is insertable within the aiming tube casing 11 with relatively close radial tolerance. For the guiding of the bore wire 3 there is provided on the casing body 21 an entryway guide 22 and an exitway guide 23. The entryway guide 22 is provided with a segment having a somewhat larger outer diameter forming a shoulder, so that the depth of insertion into the aiming tube casing 11 is limited by abutment of the shoulder. The exitway guide 23 is conically tapered towards the front, so that its insertion into the aiming tube casing 11 is facilitated.

In FIG. 1 there is further shown a milling cutter 4, of which the milling tube 41 is provided with a milling head 42. The milling tube 41 has an outer diameter which makes it possible to slide the milling cutter 4 into the guide tube casing 11, without however there being any hinderance to the rotating motion necessary for the milling process. A knurled wheel 43 is provided at one end for the operation of the milling cutter 4.

Figure 3:
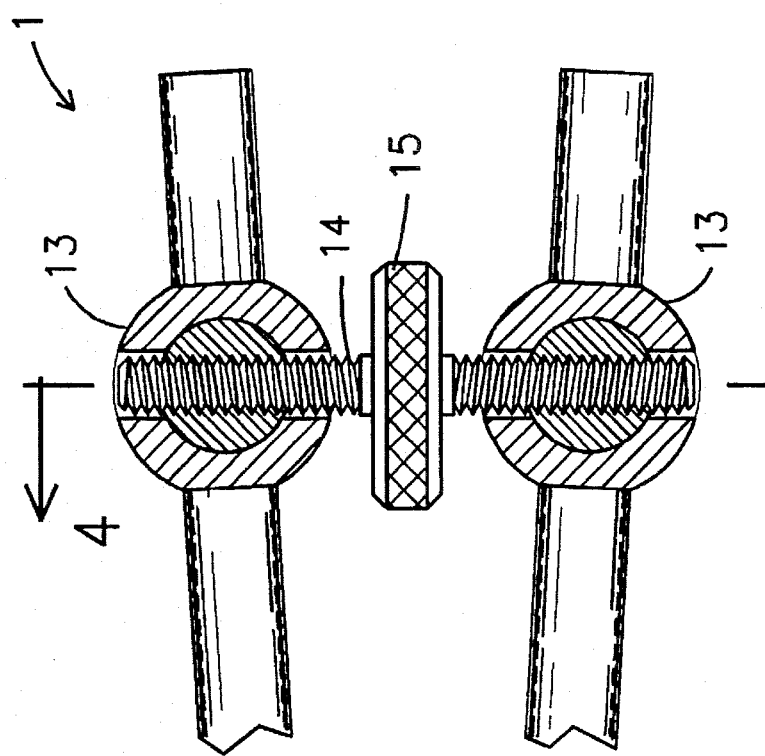

FIG. 1b shows the same aiming tube assembly as in FIG. 1a, but provided with compression screws 100. FIG. 3 shows a section from FIG. 1 (adjustment means), and FIG. 4 shows a cross-section 4—4 from FIG. 3.

Now that the invention has been described,
We claim:

1. A device for use in ventral screwing together of dens fractures with compression screws, said device comprising an aiming tube assembly (1), said aiming tube assembly comprising two aiming tube casings (11) which are pivotably joined by means of an articulated joint (12), said aiming tube assembly being precisely adjustable within a predetermined range of angles and by means of an adjusting means (13, 14, 15), said adjusting means comprising a threaded bolt (14) with a first and a second threaded section, the two threaded sections being counter-rotating with respect to each other, the first threaded section being in engagement with a threaded block (14) provided on one of the aiming tube casings (11), the second threaded section being in engagement with a threaded block (14) provided on the other of the aiming tube casings (11).

2. A device according to claim 1, wherein the angle between the two aiming tube casings (11) is precisely adjustable within a range of 4° to 6°.

3. A device according to claim 1, wherein a knurled wheel (15) is provided centrally on the threaded bolt (14).

4. A kit for facilitating the ventral screwing together of dens fractures with compression screws, comprising:

(a) a guiding bore wire;

(b) at least one compression screw provided with an axial bore and which operably fits coaxially over the guiding bore wire (3) and which is insertable with close radial tolerance in the aiming tube casing (11) of the aiming tube assembly (1);

(c) an aiming tube assembly (1), said aiming tube assembly comprising two aiming tube casings (11) which are pivotably joined by means of an articulated joint (12), said aiming tube assembly being precisely adjustable within a predetermined range of angles and by means of an adjusting means (13, 14, 15);

(d) a guide tube casing (2), said guide tube casing provided with an axial bore along the length thereof dimensioned to receive said bore wire (3), which guide tube casing (2) is dimensioned to be inserted in the aiming tube casing (11) of the aiming tube assembly (1) with close radial tolerance, and (e) a milling cutter (4), which is provided with an axial bore along the length thereof and operably fits coaxially over the guiding bore wire (3) and which is insertable with close radial tolerance in the aiming tube casing (11) of the aiming tube assembly (1).

* * * * *